US00PP07885P

United States Patent [19]

Fuess

[11] Patent Number: Plant 7,885

[45] Date of Patent: Jun. 16, 1992

[54] CHRYSANTHEMUM PLANT NAMED EMPIRE ASPEN

[76] Inventor: Janet S. Fuess, 9011 Red Hill Rd., New Hartford, N.Y. 13413

[21] Appl. No.: 543,383

[22] Filed: Jun. 26, 1990

[51] Int. Cl.[5] ..... A01H 5/00
[52] U.S. Cl. ..... Plt./74
[58] Field of Search ..... Plt./74, 75, 76, 77

[56] References Cited

U.S. PATENT DOCUMENTS

P.P. 5,240 6/1984 Jessel, Jr. et al. ..... Plt. 77

OTHER PUBLICATIONS

Bluestone Perennials, Inc. 1984 Plant Catalog, p. 10, 7211 Middle Ridge Road, Madison, Ohio 44057.

*Primary Examiner*—Howard J. Locker
*Attorney, Agent, or Firm*—Foley & Lardner

[57] ABSTRACT

A Chrysanthemum plant named Empire Aspen particularly characterized by its pure white ray floret color, compact growth habit with good spread, 7 week response period in photoperiodic programs, early natural season flowering date, free branching and flowering, and excellent keeping quality.

1 Drawing Sheet

The present invention comprises a new and distinct cultivar of Chrysanthemum, botanically known as *Dendranthema grandiflora,* and referred to by the cultivar name Empire Aspen.

Empire Aspen is a product of a planned breeding program which had the objective of creating new Chrysanthemum cultivars with a freely branching, compact cushion habit, early flower response, clear white daisy flowers, and suitability for production as a garden variety as well as for greenhouse culture. Such traits in combination were not present in previously available commercial cultivars.

Empire aspen was originated from a hybridization made in a controlled breeding program in New Hartford, N.Y. in September 1987. The female parent was a yellow decorative identified as A85-39, and the male parent was a yellow decorative identified as B87-2.

Empire Aspen was discovered and selected as one flowering plant within the progeny of the cross by applicant in September 1988 in a controlled environment in New Hartford, N.Y.

The first act of asexual reproduction of Empire Aspen was accomplished when vegetative cuttings were taken from the initial selection in November 1988 in a controlled environment in New Hartford, N.Y., by a technician working under formulations established and supervised by applicant.

Horticultural examination of selected units initiated in August 1989 has demonstrated that the uniqne combination of characteristics as herein disclosed for Empire Aspen are firmly fixed and are retained through successive generations of asexual reproduction.

Empire Aspen has not been observed under all possible environment conditions. The phenotype may vary significantly with variations in environment such as temperature, light intensity and daylength. The following observations, measurements and comparisons describe plants grown in Carpinteria, Calif. under greenhouse conditions which approximate those generally used in commercial greenhouse practice.

The following traits have been repeatedly observed and are determined to be basic characteristics of Empire Aspen which, in combination, distinguish this Chrysanthemum as a new and distinct cultivar:

1. Pure white ray floret color.
2. Use as a garden or greenhouse variety.
3. A multiplex daisy inflorescence type. The term "multiplex" means that Empire Aspen is not a typical single daisy type, but rather one in which several rows of ray florets are present, as shown in the photographic drawing.
4. An early natural season flowering date of late August in Carpinteria, Calif.
5. A relatively compact growth habit with good spread.
6. Fully expanded ray florets are approximately 2.5–2.8 cm. long and 0.8–1.0 cm. wide.
7. A response period of approximately 7 weeks in light/shade (photoperiodic) programs.
8. An average of 45–50 ray florets per capitulum.
9. Capitulum 5–6 cm. in diameter.
10. Freely branching and flowering.
11. Excellent keeping quality.

Of the many commercial cultivars known to the present inventor, the most similar in comparison to Empire Aspen is Hekla, disclosed in U.S. Plant Pat. No. 6,999. In comparison to Hekla, Empire Aspen has larger flowers, a more spreading habit, and better keeping qualitites. The daisy form, white ray floret color, seven week response in light/shade programs and natural season flowering date under garden mum culture are similar to those same characteristics of Hekla.

The accompanying photogaphic drawing shows typical inflorescence and foliage characteristics of Empire Aspen with colors being as nearly true as possible with illustrations of this type. The photograph accurately depicts the pure white ray floret color, but the foliage appears more blue than the true dark green foliage, the accurate color values for which appear below.

In the following description color references are made to The Royal Horticultural Society Colour Chart. The color values were determined between 1:00 and 3:00 p.m. on Mar. 13, 1990 under 4,000 foot candles at Carpinteria, Calif.

Classification:

*Botanical.—Dendranthema grandiflora* cv Empire Aspen.

*Commercial.*—Garden mum and daisy spray pot mum.

INFLORESCENCE

A. Capitulum:
*Form.*—Daisy.
*Type.*—Multiplex.
*Diameter across face.*—5–6 cm.

B. Corolla of ray florets: 45–50 florets.
*Color (general tonality from a distance of three meters).*—White, 155B.
*Color (lower surface).*—155D.
*Color (upper surface).*—155B.
*Size.*—2.5–2.8 cm. long and 0.8–1.0 cm. wide; petals entire to slightly dentate tips.

C. Corolla of disc florets: 185 florets.
*Color (mature).*—13B.
*Color (immature).*—6B.
*Size.*—0.6 cm. long and 0.15 cm. wide; 5-pointed.

D. Reproductive organs:

*Androecium.*—Present on disc florets only; 5 stamens, 0.35 cm. long; filaments separate; anther sacs attached, forming circle clasping style.
*Gynoecium.*—Ray: Style, 0.5 cm.; bifurcated; gold tipped stigma; whitish ovule, 1 mm. Disc: Style, 0.5 cm.; white ovule, 1 mm.

PLANT

A. General appearance:
*Height.*—20–30 cm. when grown in an 8" container.

B. Foliage:
*Color (lower surface).*—147B.
*Color (upper surface).*—147A.
*Size.*—5–7 cm. long and 3.5 cm. wide.
*Shape.*—5 lobed; somewhat pointed.

I claim:

1. A new and distinct cultivar of Chrysanthemum plant named Empire Aspen, as described and illustrated.

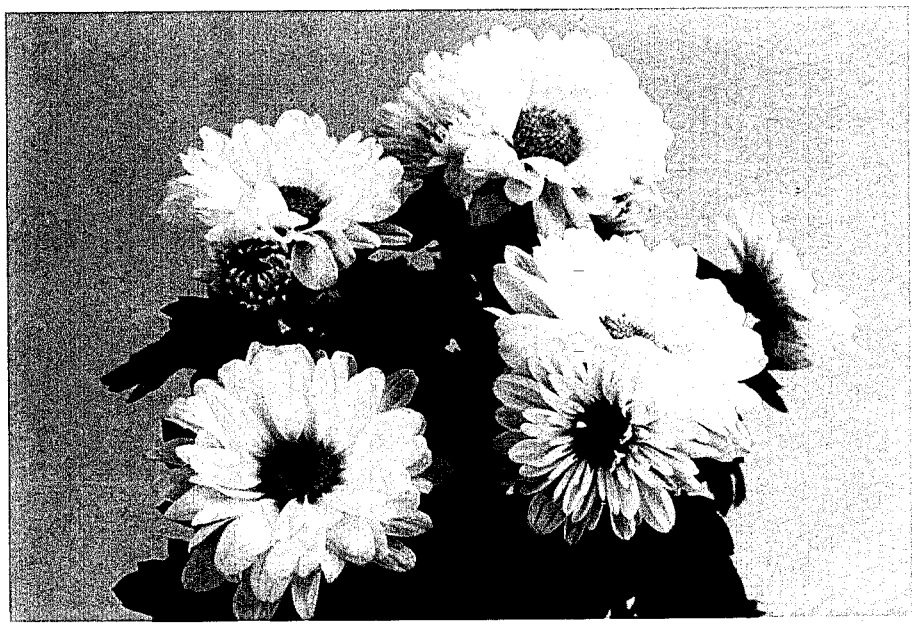

* * * * *